US012753199B2

(12) United States Patent
Shahruddin et al.

(10) Patent No.: US 12,753,199 B2
(45) Date of Patent: Oct. 6, 2026

(54) METHOD AND SYSTEM FOR PRODUCTION OF ALKYL POLYGLUCOSIDE

(71) Applicant: Petroliam Nasional Berhad (PETRONAS), Kuala Lumpur (MY)

(72) Inventors: Sara Shahruddin, Kuala Lumpur (MY); Navin Sharma Karam Chand, Kuala Lumpur (MY); Siti Fatihah Salleh, Kuala Lumpur (MY); Jofry Othman, Kuala Lumpur (MY); Nur Amalina Samsudin, Kuala Lumpur (MY)

(73) Assignee: PETROLIAM NASIONAL BERHAD (PETRONAS), Kuala Lumpur (MY)

( * ) Notice: Subject to any disclaimer, the term of this patent is extended or adjusted under 35 U.S.C. 154(b) by 614 days.

(21) Appl. No.: 18/248,092

(22) PCT Filed: Oct. 7, 2021

(86) PCT No.: PCT/MY2021/050086
§ 371 (c)(1),
(2) Date: Apr. 6, 2023

(87) PCT Pub. No.: WO2022/075836
PCT Pub. Date: Apr. 14, 2022

(65) Prior Publication Data

US 2023/0374056 A1 Nov. 23, 2023

(30) Foreign Application Priority Data

Oct. 8, 2020 (MY) ............................ PI2020005290

(51) Int. Cl.
*C07H 1/06* (2006.01)
*C07H 15/04* (2006.01)

(52) U.S. Cl.
CPC ............... *C07H 1/06* (2013.01); *C07H 15/04* (2013.01)

(58) Field of Classification Search
CPC .................................. C07H 1/06; C07H 15/04
See application file for complete search history.

(56) References Cited

U.S. PATENT DOCUMENTS 5,234,554 A 8/1993 Müller et al.
5,633,359 A 5/1997 Beaulieu
5,858,117 A 1/1999 Morris
2007/0209987 A1 9/2007 Sears
2009/0151917 A1 6/2009 Meschke et al.
(Continued)

FOREIGN PATENT DOCUMENTS

CN 105968148 A 9/2016
CN 110372136 A 10/2019
CN 111040004 A * 4/2020 ......... B01D 11/0203
(Continued)

OTHER PUBLICATIONS

English machine translation of CN 111690021 (Year: 2020).*
(Continued)

*Primary Examiner* — Renee Robinson
(74) *Attorney, Agent, or Firm* — Troutman Pepper Locke LLP (Rochester)

(57) ABSTRACT

Provided are methods and systems for the production of alkyl polyglucoside. The methods and systems provide for improved purification that results in reduced produce degradation.

12 Claims, 2 Drawing Sheets

(56) References Cited

U.S. PATENT DOCUMENTS

2018/0328660 A1 11/2018 Rumore

FOREIGN PATENT DOCUMENTS

| | | | | | |
|---|---|---|---|---|---|
| CN | 111690021 | A | * | 9/2020 | ............. C07H 15/04 |
| CN | 113416611 | A | * | 9/2021 | ............. C07H 15/04 |
| DE | 102011105758 | A1 | | 12/2012 | |
| EP | 831288 | A2 | | 3/1998 | |
| JP | H05194574 | A | | 8/1993 | |
| KR | 10-0179519 | B1 | | 4/1999 | |
| WO | 2012/175584 | A1 | | 12/2012 | |
| WO | WO-2021255243 | A1 | * | 12/2021 | ............. C07H 15/04 |

OTHER PUBLICATIONS

English machine translation of CN 113416611 (Year: 2021).*
English machine translation of CN 111040004 (Year: 2020).*
Office Action of Related CN Patent Application No. 202180080301.8 dated May 29, 2025 (with English Translation).
International Search Report and Written Opinion from corresponding PCT/MY2021/050086, mailed Feb. 8, 2022 (7 Pages).
Extended European Search Report (EESR) for Europe Patent Application No. 21878084.9, mailed Sep. 4, 2024.
Office Action issued for IN Patent Application No. 202317028178, dated Jul. 20, 2026.
Office Action issued for KR Patent Application No. 10-2023-7014049, dated Jul. 6, 2026 (English Translation).

* cited by examiner

METHOD AND SYSTEM FOR PRODUCTION OF ALKYL POLYGLUCOSIDE

CROSS-REFERENCE TO RELATED APPLICATIONS

This application is a U.S. National Phase Application of PCT International Application No. PCT/MY2021/050086, filed 7 Oct. 2021 which claims the benefit of priority of Malaysian patent application No. PI2020005290, filed 8 Oct. 2020, the contents of each being hereby incorporated by reference in their entirety for all purposes.

FIELD OF INVENTION

The present invention relates to a method and system for the production of alkyl polyglucoside.

BACKGROUND

The listing or discussion of a prior-published document in this specification should not necessarily be taken as an acknowledgement that the document is part of the state of the art or is common general knowledge.

Alkyl polyglucosides (APGs) are non-ionic surfactants that are used in variety of applications, for example cosmetics, laundry detergents and industrial cleaning. APGs are derived from glucose and fatty alcohols, and are therefore desirable because they are highly biodegradable. The production of APGs typically involves three main stages. A glycosylation step in the presence of a large excess of alcohol, purification of the APG product (including removal of the excess alcohol), and post-treatment steps such as dissolution and pH/colour adjustment.

A problem associated with the production of APGs is that they have a high melting point and viscosity, but are also prone to thermal degradation and oxidation at high temperatures. These properties cause challenges during the production of APGs, particularly during the purification stage.

Typically, purification of an APG will involve the use of falling film evaporator to remove the bulk of the fatty alcohols left over from the glycosylation step, followed by a mechanically agitated thin film evaporator (also known as a wiped-film evaporator) to remove the remaining fatty alcohol and isolate the APG product. A vacuum is typically used during evaporation since a lower operating pressure reduces the boiling point of the liquids to be evaporated, enabling lower temperatures to be used than would be required at standard pressure.

The first evaporation step using falling film evaporator is performed to remove most of the fatty alcohol solvent from the APG product. Falling film evaporators are vertical tubular evaporators that rely upon gravity to allow free flow of a thin fluid feed from the top of the unit down to the bottom where the concentrate is collected. The evaporation occurs on the surface of the falling liquid film which is highly turbulent. Separation of entrained liquid from the vapor is usually accomplished in a column connected to the bottom unit. The falling film unit is well suited to remove large volumes of diluents (there can typically be 70% of alcohol solvent in an APG product sample) by virtue of its large unit size, low liquid holdup, small floor space, and good heat transfer over a wide range of conditions.

The second evaporation step using thin film evaporator is then performed on the highly viscous residue remaining to further reduce the fatty alcohol content to less than 1%. A second, higher temperature distillation will be required because the high viscosity of the residue requires a higher temperature for the fatty alcohol to evaporate. Thin film evaporator is well suited to handle viscous fluid as it has mechanical blades that generates a high rate of surface renewal and highly turbulent conditions for even extremely viscous fluids. As the APG product mixture (feed) enters the thin film evaporator, the wiper will rotate at high speed (typically several hundred rpm) to spread the process fluid and create a thin film on the surface of evaporator. The evaporator is heated to the boiling point of the fatty alcohol at vacuum (e.g. 50 milibar), which evaporates to form a gas. The gas travels to a condenser and is then condensed and collected in a distillate collection tank. Meanwhile, the residue left behind after the thin film evaporation flows down the side wall of the evaporator and is collected in a concentrate collection tank.

The one-pass, plug flow operation of a thin-film evaporator is an advantage for minimizing thermal degradation of a heat sensitive product in an evaporation step. A variety of standard thin-film evaporator designs are commercially available, including short path distillation which has a built-it condenser in its evaporation chamber. This configuration shortens the travelling distance of the gas from the evaporator surface to the condenser, thus reducing the residence time and the chances of breakdown or oxidation of the distillate.

Despite the use of a vacuum, the high operating temperatures required inevitably result in a degree of product degradation and discolouration. APG purification using a thin-film evaporator also results in high costs for the process because thin-film evaporators are generally precision machines and therefore are more expensive than other types, particularly so if compared strictly on equivalent heat transfer area. Furthermore, short path distillation is prone to internal build-up of residue within the evaporator and require regular maintenance. The overall system comprises multiple connected parts such as valves and flanges which are susceptible to leaks. These moving parts and multiple connections require regular and periodic maintenance, adding to the overall cost of the process. Finally, the system also requires the use of expensive gear pumps to discharge the high viscosity residue.

As such, there is a need for a purification method that involves a reduced operating temperature and a lower process cost.

SUMMARY OF INVENTION

The present inventors have surprisingly found that a plate heat exchanger may be used in place of the thin film and short path distillation apparatus in the purification process. Plate heat exchangers have a number of advantages over the conventional thin film evaporator and short path distiller used in the art.

- A plate heat exchanger provides high heat transfer coefficients.
- A plate heat exchanger allows for a highly customisable heat transfer area due to the flexibility with plate size, corrugation pattern and pass arrangement.
- A plate heat exchanger can be easily dismantled for cleaning, inspection and maintenance.
- A plate heat exchanger provides high shear rates and stresses, high turbulence and mixing, and low fouling of the plates. This means a plate heat exchanger is well suited to handling highly viscous streams such as APG.
- Plate heat exchangers are cheaper than the conventionally used apparatus.

A plate heat exchanger also allows for effective separation of APG from fatty alcohol with only a single separation step, rather than multiple evaporation or distillation steps.

Thus, the present invention provides the following.

1. A method for removing at least one impurity from a stream comprising alkyl polyglucoside, said method comprising the steps of:

(i) providing a first fluid stream comprising alkyl polyglucoside and at least one impurity in the liquid phase; and (ii) passing the first fluid stream comprising alkyl polyglucoside and at least one impurity through a plate heat exchanger, wherein in step (ii) a second fluid stream is simultaneously passed through the plate heat exchanger, the second fluid stream being fluidly isolated from the first fluid stream, and thermal energy is transferred from the second fluid stream to the first fluid stream, thereby increasing the temperature of the first fluid stream to form a heated first fluid stream having a temperature above a boiling point of at least one impurity in the first fluid stream, such that the heated first fluid stream comprises a liquid phase comprising the alkyl polyglucoside and a gaseous phase comprising the at least one impurity and the gaseous phase is separated from the liquid phase.

2. The method according to Clause 1, wherein the at least one impurity comprises one or more fatty alcohols.

3. The method according to Clause 2, wherein the one or more fatty alcohols comprises a fatty alcohol having from 4 to 26 carbon atoms, for example from 8 to 20 carbon atoms, such as from 10 to 16 carbon atoms, e.g. 12 carbon atoms.

4. The method according to any one of the preceding clauses, wherein the second fluid stream comprises steam.

5. The method according to any one of the preceding clauses, wherein the first fluid stream enters the plate heat exchanger at a temperature of from about 60° C. to about 100° C., optionally from about 70° C. to about 90° C., such as about 80° C.

6. The method according to any one of the preceding clauses, wherein the second fluid stream enters the plate heat exchanger at a temperature of from about 160 to about 200° C., optionally from about 170° C. to about 190° C., such as about 180° C.

7. The method according to any one of the preceding clauses, wherein the first fluid stream is heated by the second stream to a temperature of from about 125° C. to about 165° C., such as from about 140° C. to about 155° C.

8. The method according to any one of the preceding clauses, wherein the first fluid stream is subjected to a pressure of from about 0.1 to 10 kPa in the plate heat exchanger, optionally a pressure of from about 0.5 to about 5 kPa.

9. The method according to any one of the preceding clauses, wherein one or more of the following apply:

(a) the at least one impurity comprises one or more fatty alcohols;

(b) the first fluid stream is heated by the second fluid stream to a temperature of from about 110° C. to about 170° C.; and (c) the first fluid stream is subjected to a pressure of from about 0.1 to 10 kPa in the plate heat exchanger.

10. The method according to any one of the preceding clauses, further comprising a step of condensing and collecting the at least one impurity present in the separated gas phase of the first fluid stream after step (i).

11. The method according to any one of the preceding clauses, wherein the separation of the heated first stream is achieved by passing the heated first stream into a flash tank having a greater internal volume than the plate heat exchanger, to separate the gaseous phase comprising the at least one impurity from the liquid phase comprising the alkyl polyglucoside.

12. The method according to Clause 11, wherein the pressure inside the flash tank is lower than the pressure of the heated first fluid stream entering said tank, optionally wherein the pressure inside the flash tank from about 1 kPa to about 3 kPa.

13. A system for purifying alkyl polyglucoside, said system comprising a plate heat exchanger configured to heat a first fluid stream comprising alkyl polyglucoside and at least one impurity to a temperature above the boiling point of the at least one impurity.

DRAWINGS

Figure 1:
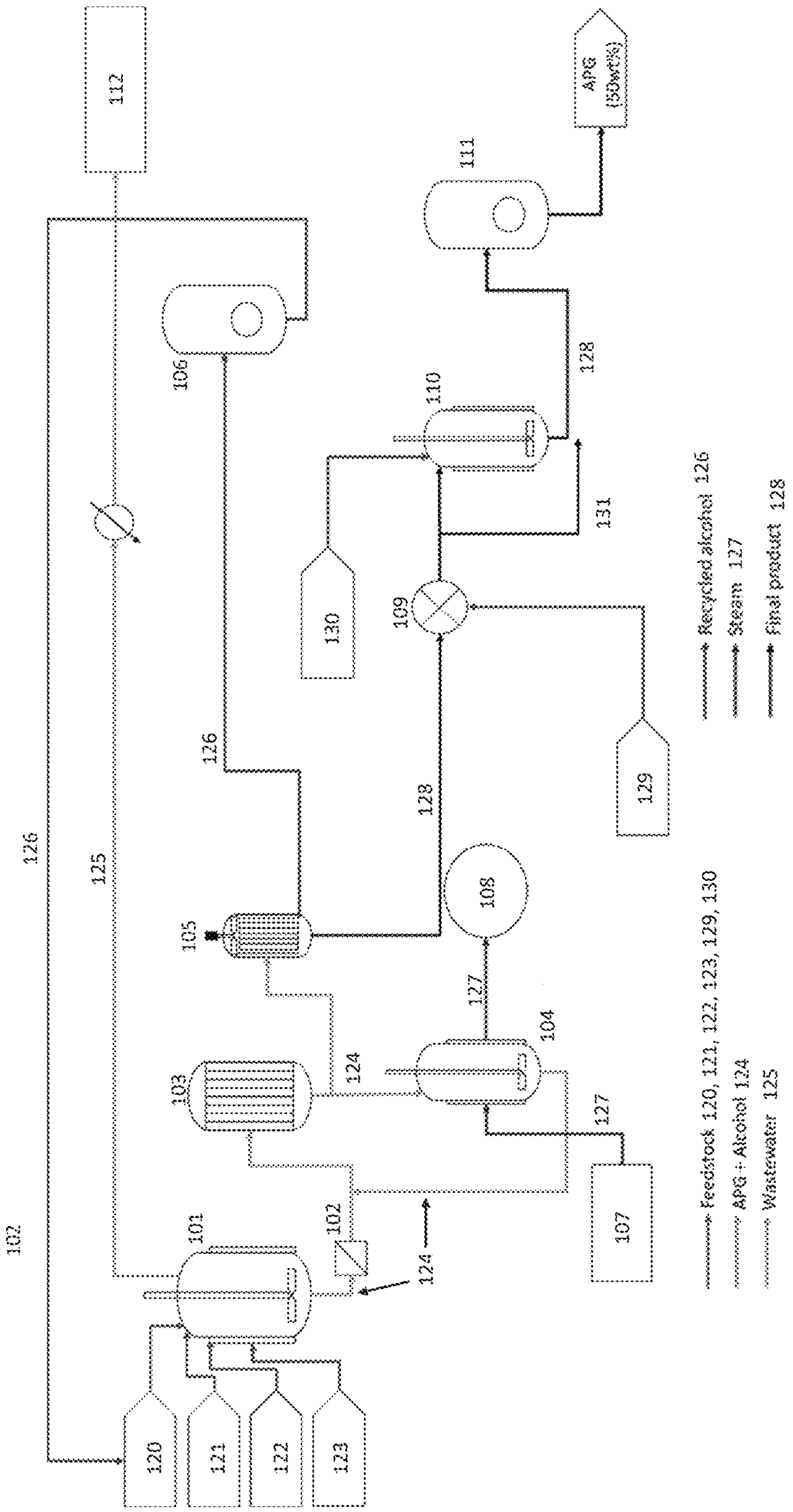
FIG. 1 shows a process flow diagram of a conventional APG production system, in which the APG is purified using a falling film evaporator and short path distiller.

Certain embodiments of the present disclosure are described more fully hereinafter with reference to the accompanying drawings.

DESCRIPTION

The invention provides a method for removing at least one impurity from a stream comprising alkyl polyglucoside during the alkyl polyglucoside production process.

Alkyl polyglucoside is typically produced on a commercial scale using the Fischer glycosylation. This process involves direct glycosylation and transglycosylation to produce an acetal linkage between the glucose sugar headgroup and a fatty alcohol hydroxyl group. The process is generally a batch process, in which fatty alcohol (typically lauryl alcohol) is pumped to a reactor, where it is stirred and heated. During the heating process, dextrose (typically in the form of an anhydrous solid) is fed into the reactor. Proper mixing is required to ensure good dispersion of solid particles in the solution. When the reaction mixture reaches a temperature of about 110° C. to 115° C., a dodecyl benzenesulfonic acid (DBSA) catalyst is added to the reactor. The reaction is carried out at about 110° C. under a pressure of from about 3 to about 5 kPa, for approximately 4 hours. During the reaction, alkyl polyglucosides (APG) having various degree of polymerisation are produced, together with water (as water vapour). The water vapour is simultaneously removed to improve the yield of the reaction. This vapour stream is generally discharged from the top of reactor and comprises both water and evaporated fatty alcohol, and is passed into a cooler where it is partially condensed. The collected fatty alcohol may be recycled as feedstock for the next batch of the process. The remaining vapour stream, which is predominantly water, may be further condensed to form liquid water which can be sent to a wastewater treatment plant.

Once the reaction has run to completion, the reactor temperature is reduced to approximately 70° C. and the pressure increased to atmospheric pressure. The reaction mixture is neutralised inside the reactor, for example by addition of sodium hydroxide. The final pH of the solution is generally adjusted to a value of about 8 to 10. The product stream comprises roughly 25% APG, and must be purified.

A preliminary purification may involve filtering to remove solid impurities such as unreacted dextrose, and the by-products polydextrose and sodium laurylbenzenesulfonate. Subsequent purification steps are performed on the liquid crude reaction product.

The invention provides a method that is useful in the purification of the liquid crude reaction product comprising APG. Specifically, the invention provides a method for removing at least one impurity from a stream comprising alkyl polyglucoside, said method comprising the steps of:

(i) providing a first fluid stream comprising alkyl polyglucoside and at least one impurity in the liquid phase; and (ii) passing the first fluid stream comprising alkyl polyglucoside and at least one impurity through a plate heat exchanger, wherein in step (ii) a second fluid stream is simultaneously passed through the plate heat exchanger, the second fluid stream being fluidly isolated from the first fluid stream, and thermal energy is transferred from the second fluid stream to the first fluid stream, thereby increasing the temperature of the first fluid stream to form a heated first fluid stream having a temperature above a boiling point of at least one impurity in the first fluid stream, such that the heated first fluid stream comprises a liquid phase comprising the alkyl polyglucoside and a gaseous phase comprising the at least one impurity and the gaseous phase is separated from the liquid phase.

As used herein, alkyl polyglucoside (APG) means a chemical comprising polyglucoside moiety attached to an alkyl moiety. The polyglucoside moiety is attached to the alkyl moiety by a C—O bond formed from a carbon atom in the alkyl chain and an exocyclic oxygen atom in the polyglucoside.

As used herein, a polyglucoside is a moiety formed from multiple glucose rings that are connected by glycosidic bonds. A wide range of number average molecular weights may be produced, depending on the desired use of the polyglucoside. The polyglucoside typically has a number average molecular weight of from 100 to 5000 Daltons, from 200 to 2000 Daltons, from 250 to 1000 Daltons, or from 300 to 600 Daltons.

The alkyl group in an alkyl polyglucoside typically comprises from 4 to 26 carbon atoms, for example from 8 to 20 carbon atoms, such as from 8 to 16 carbon atoms, e.g. 10 to 14 carbon atoms. In a particular embodiment of the invention, the alkyl group in an alkyl polyglucoside may comprise 12 carbon atoms.

The chain length of the alkyl group influences the properties of the APG, and different chain lengths may be appropriate for different uses. For example, a C12 or C14 chain length may be appropriate for personal care applications (e.g. cosmetics, bath products, cleansers, wipes, and oral care products), and for homecare applications (e.g. surface cleaners, dishwashing agents, and laundry detergents). A C8 or C10 chain length may be appropriate for hard surface cleansers, agrochemicals and industrial cleaning products.

As used herein, "removing" an impurity refers to reducing the amount of said impurity in a product stream, for example a product stream comprising APG. The impurity may be reduced to an amount of no more than 10 wt %, 9 wt %, 8 wt %, 7 wt %, 6 wt %, 5 wt %, 4 wt %, 3 wt %, 2 wt %, 1 wt %, 0.5 wt %, or 0.1 wt % of the product stream. Typically, the impurity will be removed such that it comprises less than 1 wt % of the product stream.

As used herein, an "impurity" refers to a chemical present in a product stream other than the desired product and water. Thus, when the product stream comprises APG as a desired product, an impurity in said product stream refers to any chemical present in the product stream other than APG or water. In some embodiments of the invention, the impurity may be one or more fatty alcohols.

As used herein, a fatty alcohol refers to a compound comprising a hydrophobic hydrocarbon portion and an alcohol functional group. The hydrocarbon portion may be saturated (i.e. an alkyl group) or unsaturated (e.g. an alkenyl group, or a group comprising two or more C═C double bonds, such as a dienyl or trienyl group). For example, the fatty alcohol may comprise an alkyl or alkenyl group attached to an alcohol group. In general, a fatty alcohol may comprise from 4 to 26 carbon atoms, for example from 8 to 20 carbon atoms, such as from 8 to 16 carbon atoms, e.g. 10 to 14 carbon atoms. In a particular embodiment of the invention, the alkyl group in the fatty alcohol may comprise 12 carbon atoms. Typically, the fatty alcohol comprises a linear (i.e. unbranched) carbon chain attached to a primary alcohol group.

As used herein, the "boiling point" of a chemical when used in the context of a method step refers to the lowest temperature at which the chemical will evaporate under the conditions to which it is subjected. Certain conditions, such as pressure or the presence of other components in the stream, may affect the boiling point of a chemical. Thus, if the chemical is subject to a reduced pressure, then its boiling point will be lower than the boiling point at standard pressure. Specifically, the boiling point of an impurity present in the first stream when within the plate heat exchanger will be lower than its boiling point at standard pressure.

Similarly, and as will be appreciated by a person skilled in the art, the boiling point of a chemical present in the mixtures disclosed herein may be higher or lower than the expected boiling point of said chemical in isolation. This is because the boiling point may be elevated or depressed due to the presence of the other components of the mixture. Thus, when used herein, the boiling point of a chemical (such as an impurity) is intended to refer to the boiling point of the chemical when in a mixture disclosed herein.

When the first fluid stream is heated to a temperature above the boiling point of the at least one impurity, the at least one impurity will evaporate and enter the gas phase, forming a gaseous phase alongside the liquid phase within the first stream. This gaseous phase can be easily separated from the liquid phase and passed to a condenser to collect the at least one impurity. This is desirable when the at least one impurity comprises a useful chemical such as unreacted fatty alcohol. In this case, the fatty alcohol may be collected and used in the production of further alkyl polyglucoside.

In order to assist the separation of gas and liquid phases within the plate heat exchanger, the plate heat exchanger may be designed to operate as falling film evaporator, in which a chamber is put in place at the bottom of the tubes providing the needed vapor-liquid-equilibrium headspace.

The separation of the liquid first stream from the gas phase impurity may be performed in a flash tank. Thus, the heated liquid first stream and gas phase impurity are passed into a flash tank having a higher volume than the space inside the plate heat exchanger. This higher volume allows the liquid phase that contains APG to collect at the bottom of the flash tank, while the gas phase can be siphoned off at the top of the tank. As would be understood by a person skilled in the art, the pressure inside the flash tank may be the same as, but typically is lower than, that inside the plate heat exchanger, for example from about 1 kPa to about 3 kPa, e.g. about 2 kPa.

The purified APG residue, which is highly viscous, may be mixed with water to facilitate further processing.

The first stream is heated within the heat exchanger by a second stream that is fluidly isolated from the first stream, but which is able to transfer thermal energy through the heat exchanger to the first stream. The second stream may comprise, or consist of, steam that has been heated to a temperature suitable for raising the temperature of the first stream to a desired temperature. For example, the second stream may enter the heat exchanger at a temperature of from about 160 to about 200° C., optionally from about 170° C. to about 190° C., such as about 180° C.

In order to increase the efficiency of the heat exchanger, the first stream is typically pre-heated before entering the heat exchanger, such that the difference in temperature between the first and second streams is not excessively high. Thus, the first stream may enter the heat exchanger having a temperature of from about 60° C. to about 100° C., optionally from about 70° C. to about 90° C., such as about 80° C.

It is hereby explicitly contemplated that the end point of any range disclosed herein may be combined with the end point of any other range for the same variable. As an illustrative example using the ranges for the temperature of the first stream entering the heat exchanger, there is disclosed a temperature range of:

from about 60° C. to about 70° C., from about 60° C. to about 80° C., from about 60° C. to about 90° C., and from about 60° C. to about 100° C.;

from about 70° C. to about 80° C., from about 70° C. to about 90° C., and from about 70° C. to about 100° C.;

from about 80° C. to about 90° C., and from about 80° C. to about 100° C.; and from about 90° C. to about 100° C.

The below Examples illustrate the invention, and are not to be construed as limitative.

EXAMPLES

Reference Example: Synthesis of APG

APGs may be synthesised by Fischer glycosylation in a batch reaction. Lauryl alcohol may be added to a reactor with stirring and heating, followed by addition of anhydrous. The mixture is stirred to ensure good dispersion of solid particles in the solution. Once the reaction mixture reaches a temperature of from 110° C. to 115° C., dodecyl benzenesulfonic acid (DBSA) catalyst is added. The reaction mixture is stirred at 110° C., under a pressure of from 3 to 5 5 kPa for 4 hours. Water vapour is continuously removed from the reactor and fed into a first condenser to collect fatty alcohol, followed by a second, lower temperature, condenser to collect liquid water.

The reaction product is alkyl polyglucosides (APG) having various degree of polymerisation. Once the reaction has run to completion, the reactor temperature is reduced to approximately 70° C. and the pressure is increased to atmospheric pressure. The pH of the reaction mixture is adjusted to 8-10 with 5 wt % sodium hydroxide solution. The reaction mixture comprises approximately 25% of APG, and is then pumped into a cyclone to filter out the unreacted dextrose and the by-products polydextrose and sodium laurylbenzenesulfonate. A crude product comprising APG is obtained.

Comparative Example: Conventional Purification Process

The crude product may be purified using the apparatus shown in FIG. 1, in which the components are as follows.

| Component | Reference numeral | Chemical stream | Reference numeral |
|---|---|---|---|
| 101 | Reactor | 120 | Fatty alcohol |
| 102 | Filter | 121 | Dextrose |
| 103 | Falling film evaporator | 122 | Catalyst |
| 104 | Falling film holding tank | 123 | NaOH |
| 105 | Thin film evaporator | 124 | APG + alcohol |
| 106 | Recycled alcohol holding tank | 125 | Wastewater |
| 107 | Electric steam boiler | 126 | Recycled alcohol |
| 108 | Steam trap | 127 | Steam |
| 109 | In-line mixer | 128 | Final product |
| 110 | Mixing tank | 129 | Water and NaOH |
| 111 | Product holding tank | 130 | 30 wt. % hydrogen peroxide solution |
| 112 | Wastewater treatment plant | 131 | Final product bypass line if no bleaching is required |

Before entering the falling film evaporator 103 (FFE), the product stream 124 coming from cyclone filter will pass through heaters (not shown) and be preheated to approximately 135° C. It then enters the falling film evaporator 103 (FFE). The desired working temperature, pressure and flow rate of FFE are approximately 165° C., 1 kPa and 0.6 to 8 m/s. Inside the FFE, the product stream flows through the internal tubes which are heated by external steam. Part of the fatty alcohol and water are evaporated and passed to a condenser to collect the fatty alcohol, which can be recycled for future batches. The residue exiting the bottom of the FFE is then transferred through a heat exchanger 103 before entering the short path distiller 105. The desired working temperature, pressure and flow rate of the short path distiller are approximately 170° C. (evaporator and residue line), 0.05-0.1 kPa (oscillating), 0.7 L/h feed rate, 300 rpm agitator speed.

Fatty alcohol in the product stream will be evaporated, after which it is condensed and collected for re-use (see recycled alcohol stream 126). Meanwhile, the distilled APG is collected and mixed with water immediately before sent into a holding tank 111. The stream entering the holding tank consists of approximate 50 wt % of APG in water with less than 1% of fatty alcohol.

Working Example: Purification Process Using a Plate Heat Exchanger

Figure 2:
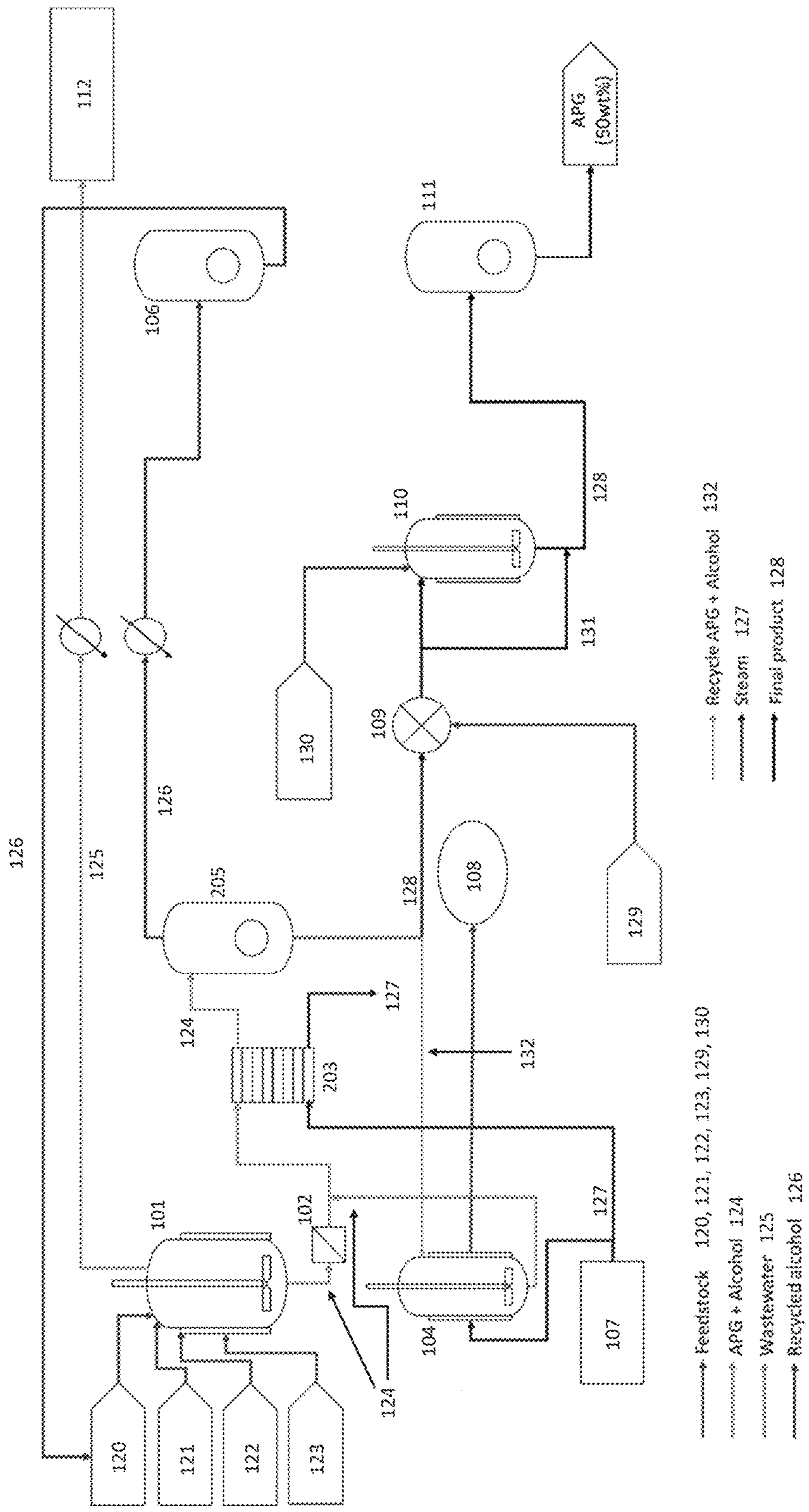
FIG. 2 shows a process flow diagram of an APG production system according to the invention, in which the APG is purified using plate heat exchanger.

The crude product may be purified using the apparatus and method of the invention shown in FIG. 2, in which the components are as follows.

| Component | Reference numeral | Chemical stream | Reference numeral |
|---|---|---|---|
| 101 | Reactor | 120 | Fatty alcohol |
| 102 | Filter | 121 | Dextrose |
| 203 | Plate heat exchanger | 122 | Catalyst |

-continued

| Component | Reference numeral | Chemical stream | Reference numeral |
|---|---|---|---|
| 104 | Plate heat exchanger holding tank | 123 | NaOH |
| 205 | Flash tank | 124 | APG + alcohol |
| 106 | Recycled alcohol holding tank | 125 | Wastewater |
| 107 | Electric steam boiler | 126 | Recycled alcohol |
| 108 | Steam trap | 127 | Steam |
| 109 | In-line mixer | 128 | Final product |
| 110 | Mixing tank | 129 | Water and NaOH |
| 111 | Product holding tank | 130 | 30 wt. % hydrogen peroxide solution |
| 112 | Wastewater treatment plant | 131 | Final product bypass line if no bleaching is required |
| | | 132 | Recycled APG and alcohol |

The product stream 124 from the reactor 101 is passed through heaters (not shown) to preheat the stream to approximately 80° C. before it enters the PHE 203 via the cold fluid inlet. Meanwhile, steam 127 as the working fluid will enter at the hot fluid inlet. The heat duty of the PHE is approximately 0.5 kW. The arrangement of the gaskets is such that it allows the product stream to spread over one plate, while the steam spreads over the adjacent plate. The desirable working temperature, pressure and flow rate of the two streams are shown in Table 1.

TABLE 1

Plate Heat Exchanger Operating Conditions

| Plate Heat Exchanger Operating Conditions | Hot channel | Cold channel |
|---|---|---|
| 2. Fluid | Steam | APG |
| 3. Inlet temperature (° C.) | 180 | 80 |
| 4. Outlet temperature (° C.) | 120 | 125-165 |
| 5. Flow rate (L/h) | 1 | 0.5-1 |
| 6. Maximum working pressure (Mpag) | 0.2 | 0.005 |

Inside the PHE 203 (which exists at a high temperature and low pressure), part of the fatty alcohol and water in the product stream are evaporated, such that the stream comprises a gaseous phase comprising fatty alcohol and water vapour, and a liquid phase comprising APG and any unevaporated fatty alcohol/water. To enable effective separation of entrained liquid from the vapor, plate type heat exchangers can be designed to operate as falling film evaporator, in which a chamber is put in place at the bottom of the tubes providing the needed vapor-liquid-equilibrium headspace. The stream is then passed into a flash tank 205, where the APG is separated from the evaporated fatty alcohol and water. The flash tank may be subject the same pressure and temperature as the plate heat exchanger, but is typically subject to a decreased pressure (e.g. a pressure of about 1 kPa to about 3 kPa, such as about 2 kPa). The fatty alcohol vapor will exit as distillates or top product 126 and will be condensed and pumped into a holding tank 106 to be recycled as feedstock for next batch of reaction. Meanwhile, the purified APG residue 128 will exit as a bottom product and can be pumped out and mixed with water and NaOH 129 to facilitate further processing. If desired, the product stream 128 may be bleached with hydrogen peroxide 130 in mixing tank 110. If bleaching is not required, the mixing tank may be bypassed with line 131. The final APG stream may consist of approximately 50 wt % of APG in water with less than 1% of fatty alcohol, since such a stream is much easier to handle than an APG residue that does not comprise water.

If the stream exiting the plate heat exchanger requires further separation, the APG and alcohol 132 may be passed into a holding tank 104 and then back into the plate heat exchanger 203.

As demonstrated in this Example, an advantage associated with the use of the PHE to separate APG from fatty alcohol is that an effective separation may be achieved without requiring multiple distillation steps, as is required in prior art processes utilising agitated evaporation and short path distillation techniques.

The invention claimed is:

1. A method for removing at least one impurity from a stream comprising alkyl polyglucoside, said method comprising the steps of:

(i) providing a first fluid stream comprising alkyl polyglucoside and at least one impurity; and (ii) passing the first fluid stream comprising alkyl polyglucoside and at least one impurity through a plate heat exchanger, wherein in step (ii) a second fluid stream is simultaneously passed through the plate heat exchanger, the second fluid stream being fluidly isolated from the first fluid stream, and thermal energy is transferred from the second fluid stream to the first fluid stream, thereby increasing the temperature of the first fluid stream to form a heated first fluid stream having a temperature above a boiling point of at least one impurity in the first fluid stream, such that the heated first fluid stream comprises a liquid phase comprising the alkyl polyglucoside and a gaseous phase comprising the at least one impurity and the gaseous phase is separated from the liquid phase.

2. The method according to claim 1, wherein the at least one impurity comprises one or more fatty alcohols.

3. The method according to claim 2, wherein the one or more fatty alcohols comprises a fatty alcohol having from 4 to 26 carbon atoms.

4. The method according to claim 1, wherein the second fluid stream comprises steam.

5. The method according to claim 1, wherein the first fluid stream enters the plate heat exchanger at a temperature of from about 60° C. to about 100° C.

6. The method according to any claim 1, wherein the second fluid stream enters the plate heat exchanger at a temperature of from about 160 to about 200° C.

7. The method according to claim 1, wherein the first fluid stream is heated by the second stream to a temperature of from about 125° C. to about 165° C.

8. The method according to claim 1, wherein the first fluid stream is subjected to a pressure of from about 0.1 to 10 kPa in the plate heat exchanger.

9. The method according to claim 1, wherein one or more of the following apply:

(a) the at least one impurity comprises one or more fatty alcohols;

(b) the first fluid stream is heated by the second fluid stream to a temperature of from about 110° C. to about 170° C.; and (c) the first fluid stream is subjected to a pressure of from about 0.1 to 10 kPa in the plate heat exchanger.

10. The method according to claim 1, further comprising a step of condensing and collecting the at least one impurity present in the separated gas phase of the first fluid stream after step (i).

11. The method according to claim 1, wherein the separation of the heated first stream is achieved by passing the heated first stream into a flash tank having a greater internal volume than the plate heat exchanger, to separate the gaseous phase comprising the at least one impurity from the liquid phase comprising the alkyl polyglucoside.

12. The method according to claim 11, wherein the pressure inside the flash tank is lower than the pressure of the heated first fluid stream entering said tank.

* * * * *